US00PP28602P3

(12) United States Plant Patent
Olesen

(10) Patent No.: US PP28,602 P3
(45) Date of Patent: Nov. 7, 2017

(54) ***CLEMATIS* PLANT NAMED 'EVIPO067'**

(50) Latin Name: *Clematis viticella*
Varietal Denomination: Evipo067

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 42 days.

(21) Appl. No.: 14/756,242

(22) Filed: Aug. 20, 2015

(65) Prior Publication Data

US 2017/0055411 P1 Feb. 23, 2017

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Poulsen Roser A/S, Perfection by Poulsen, Jan. 2013.*

* cited by examiner

*Primary Examiner* — Keith Robinson

(57) ABSTRACT

A new *Clematis* plant with a compact growth habit, profuse, violet blue flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo067'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2002 and the resulting seeds were planted the following winter in a controlled environment in Guernsey, Channel Islands, United Kingdom. The new variety named 'Evipo067' originated as a single seedling from the stated cross.

The new *clematis* plant may be distinguished from its female seed parent and male pollen parent by the following characteristics. The male pollen parent attains 50 to 60 cm in growth height, while the new variety attains 40 to 50 cm in growth in one season. The female seed parent has flowers which are Violet Group 85D while the new variety has flowers which are Violet-Blue Group 90D.

The objective of the hybridization of this *clematis* plant was to create a new and distinct variety for nursery culture with unique qualities such as:

1. Uniform and abundant violet blue flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo067' was selected by Mogens N. Olesen and Raymond J. Evison in their *clematis* development program in the Channel Islands, United Kingdom in 2003. Asexual reproduction of 'Evipo067' by means of vegetative stem cuttings and traditional layering was first performed by Mogens N. Olesen and Raymond J. Evison in the nursery during the summer of 2003. This initial and subsequent asexual propagations have demonstrated that the characteristics of 'Evipo067' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo067'. Specifically illustrated are flowers at various stages of development, flower in parts, tepals detached, leaves, and stems. Plants shown are 2 years of age.

DETAILED DESCRIPTION Of THE VARIETY

The following is a detailed description of 'Evipo067', as observed in its growth throughout the flowering period in Fredensborg Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo017' described and illustrated in U.S. Plant Pat. No. 15,163 are compared to 'Evipo067' in Chart 1.

CHART 1

| | 'Evipo067' | 'Evipo017' |
|---|---|---|
| Flower diameter | 110 mm | 100 to 130 mm |
| Tepal upper surface upon opening | Violet-Blue Group 90D | Violet Group 85A with intonations of Violet Group 85D |
| Tepal count | 8 | 8 |

FLOWER AND FLOWER BUD

Blooming habit: Continuous. The natural flowering period is generally from May to September.

Flower bud:
- *Size*.—Normally 30 mm in length. Bud diameter is 12 mm.
- *Bud form*.—Long elliptic.
- *Bud color*.—At ¼ opening tepals are Violet-Blue Group 90C.

Peduncle:
- *Surface texture*.—Pubescent.
- *Length*.—40-55 mm.
- *Color*.—Yellow-Green Group 146B.
- *Strength*.—Moderately strong.

Receptacle:
- *Surface texture*.—Lightly pubescent.
- *Shape*.—Broad funnel.
- *Size*.—2 mm (h)×4 mm (w).
- *Color*.—Yellow-Green Group 146B.

Flower arrangement:
- *Location on vine*.—New growth only.
- *Borne*.—Singly and clusters of 3 flowers.
- *Attitude on vine*.—Upward and outward.

Flower bloom:
- *Size*.—On average, flowers are 110 mm in diameter and 20 mm in depth.
- *Profile*.—Open flowers are rotate.
- *Fragrance*.—None.
- *Lasting quality*.—Flowers normally remain up to 7 days on the plant.

Tepals:
- *Tepal color*.—Upon opening, the upper surface is Violet Group 86B. The lower surface is Violet-Blue Group 90D with a central bar of Green Group 139D. After opening, the upper surface is Violet-Blue Group 90D. The lower surface is Violet-Blue Group 90D with a central bar of Green Group 139D.
- *Quantity*.—Normally 8 tepals.
- *Size*.—About 55 mm in length by 35 mm wide.
- *Shape*.—Individual tepal shape is ovate. The tepal apex is acuminate. The tepal base is typically acute.
- *Arrangement*.—Overlapping.
- *Apex recurvature*.—Slightly curved.
- *Tepal cross section*.—Slightly reflexed.
- *Margins*.—Entire. Medium undulations of margin observed.
- *Persistence*.—Tepals drop off cleanly.

Reproductive organs:
- *Pollen coloration*.—Yellow-Green Group 158D.
- *Pollen amount*.—Moderate.
- *Anthers*.—Size: 6 mm in length. Color: Yellow Group 10A. Quantity: On average, 30.
- *Filaments*.—Color: Green-Yellow Group 1C. Length: About 11 mm.
- *Pistils*.—Quantity: On average, 60.
- *Stigmas*.—Superior in location relative to the length of the filaments and the height of the anthers.
- *Styles*.—Color: Yellow-Green Group 152D. Length: 10 mm.

Seed head characteristics:
- *Size*.—30 mm in height. 50 mm in diameter.
- *Quantity*.—The average number of seeds produced per seed head is 60.

Style appearance: Plumose.
- *Shape*.—Seed heads are globose.

PLANT

Plant form: Creeping.

Plant growth: Moderately vigorous.

Size: Seasons growth attains 40 to 50 cm of horizontal growth.

Stems:
- *Color*.—Juvenile stems are Greyed-Orange Group 165A. Mature stems are Greyed-Orange Group 166A.
- *Internodes*.—On average, 5 cm between nodes.
- *Length*.—Normally 40 cm from the base of the plant to the flowering portion of the stem.
- *Diameter*.—Normally 3 cm.
- *Texture*.—Ribbed.

Plant foliage:
- *Leaf characteristics*.—Deciduous.
- *Arrangement*.—Trifoliate.
- *Leaf size*.—Compound leaves are normally 100 mm (l)×60 mm (w). Leaflets are normally 80 mm (l)×30 mm (w).
- *Abundance*.—On average 2 leaves per 10 cm of stem.
- *Leaf color*.—Juvenile upper Yellow-Green Group 144A. Juvenile lower Yellow-Green Group 144A. Mature upper Yellow-Green Group 147A. Mature lower Yellow-Green Group 147B.
- *Stipules*.—Absent.
- *Petioles*.—Size: Normally 50 mm in length by 2 mm diameter. Texture: Lightly pubescent. Color: Yellow-Green Group 144A.
- *Petioloule*.—Size: Normally 15 to 20 mm in length by 2 mm diameter. Texture: Lightly pubescent. Color: Yellow-Green Group 144A.
- *Leaflet shape*.—Generally elliptic. The base is rounded. The apex is acute.
- *Margin*.—Entire.
- *Surface*.—The upper side is smooth. The lower side is smooth.
- *Thickness*.—Moderate.
- *Glossiness*.—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

I claim:

1. A new and distinct variety of *clematis* plant named 'Evipo067', substantially as described and illustrated , due to its abundant violet blue flowers with good keepability, attractive long lasting foliage and compact growth, year round flowering under glasshouse conditions, suitability for production from softwood cuttings in pots, durable flowers and foliage which make the variety suitable for distribution in the floral industry.

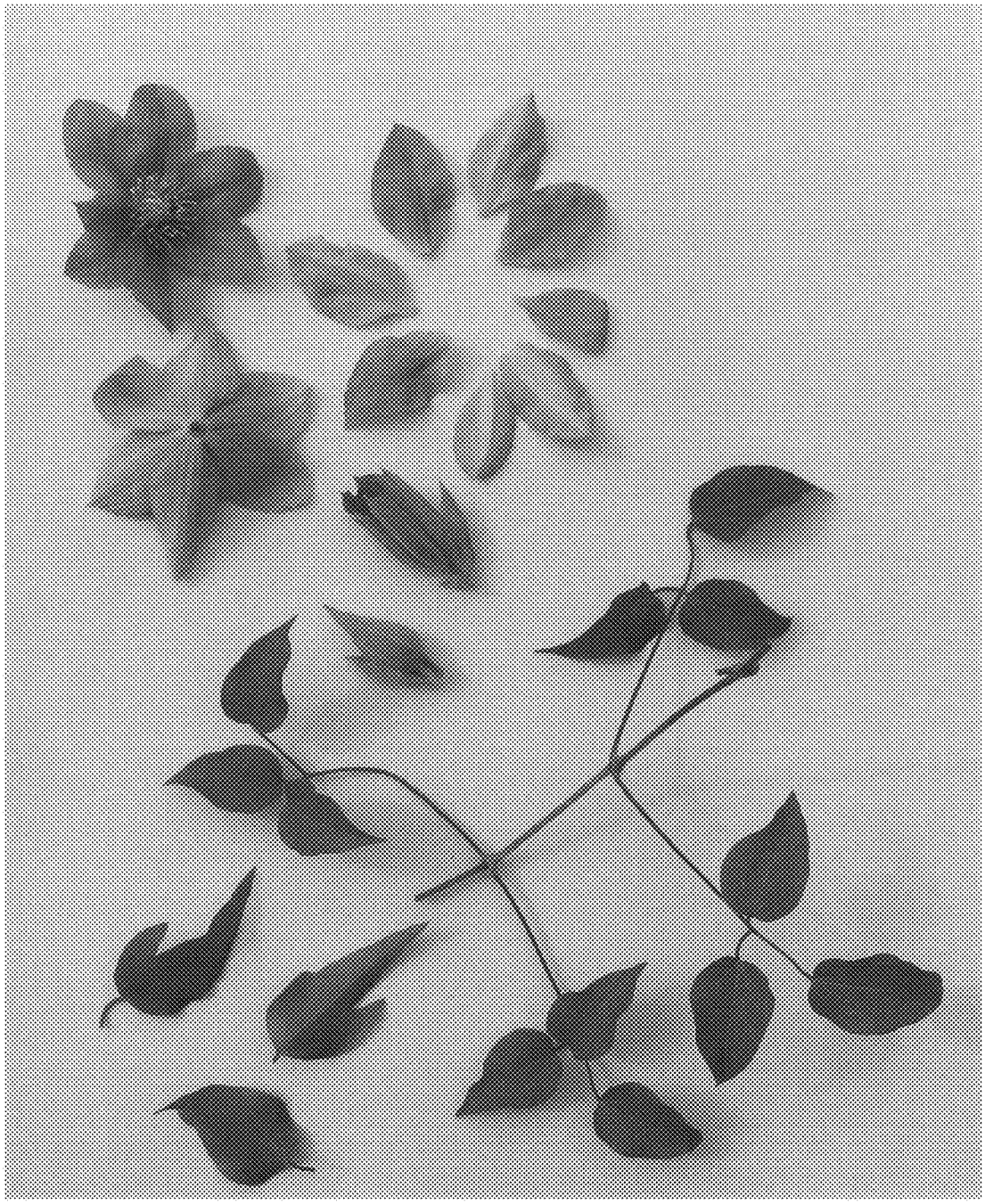

* * * * *